United States Patent
Dohil

(10) Patent No.: US 11,576,871 B2
(45) Date of Patent: Feb. 14, 2023

(54) FORMULATIONS OF CYSTEAMINE AND CYSTAMINE

(71) Applicant: The Regents of the University of California, Oakland, CA (US)

(72) Inventor: Ranjan Dohil, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 573 days.

(21) Appl. No.: 16/461,361

(22) PCT Filed: Nov. 16, 2016

(86) PCT No.: PCT/US2016/062359
§ 371 (c)(1),
(2) Date: May 15, 2019

(87) PCT Pub. No.: WO2018/093364
PCT Pub. Date: May 24, 2018

(65) Prior Publication Data
US 2020/0101022 A1    Apr. 2, 2020

(51) Int. Cl.
*A61K 9/48* (2006.01)
*A61K 9/20* (2006.01)
*A61K 9/28* (2006.01)
*A61K 31/145* (2006.01)

(52) U.S. Cl.
CPC .......... *A61K 9/4891* (2013.01); *A61K 9/2054* (2013.01); *A61K 9/282* (2013.01); *A61K 9/4866* (2013.01); *A61K 31/145* (2013.01)

(58) Field of Classification Search
None
See application file for complete search history.

(56) References Cited

U.S. PATENT DOCUMENTS

| | | |
|---|---|---|
| 2005/0245433 A1 | 11/2005 | Chan et al. |
| 2008/0020041 A1 | 1/2008 | Ayres |
| 2009/0076166 A1 | 3/2009 | Dohil et al. |
| 2012/0328671 A1 | 12/2012 | O'Neil et al. |
| 2014/0120162 A1 | 5/2014 | Methiowitz et al. |
| 2014/0199389 A1 | 7/2014 | Spading et al. |
| 2014/0370085 A1 | 12/2014 | Powell et al. |
| 2015/0011611 A1 | 1/2015 | Kim et al. |

OTHER PUBLICATIONS

Mohri Mineko, International Preliminary Report on Patentability and Written Opinion, PCT/US2016/062359, The International Bureau of WIPO, dated May 31, 2019.
Dohil et al., "Understanding Intestinal Cysteamine Bitartrate Absorption," J. of Pediatrics, vol. 148, pp. 764-769, Jun. 2006.
Mylan Pharmaceuticals Inc., http://medlibrary.org/lip.rx/meds/cystagon/page/4/, Jul. 17, 2007.
Young, Lee W., International Search Report and Written Opinion, PCT/US2016/062359, United States Patent & Trademark Office, dated Jan. 30, 2017.

*Primary Examiner* — Robert A Wax
*Assistant Examiner* — Randeep Singh
(74) *Attorney, Agent, or Firm* — Gavrilovich, Dodd & Lindsey LLP

(57) ABSTRACT

The disclosure provides cysteamine salt and cystamine formulations comprising enteric coatings. The disclosure also provides composition for use in treating diseases and disorders that can be treated with cysteamine.

22 Claims, No Drawings

FORMULATIONS OF CYSTEAMINE AND CYSTAMINE

CROSS REFERENCE TO RELATED APPLICATIONS

This is a U.S. National Phase Application filed under 35 U.S.C. § 371 and claims priority to International Application No. PCT/US2016/062359, filed Nov. 16, 2016, the disclosures of which are incorporated herein by reference.

FIELD OF THE INVENTION

The invention relates in general to compositions and methods comprising cysteamine or a salt thereof or cystamine or a salt thereof and to the use of such compositions to treat various diseases and disorders.

BACKGROUND

Cysteamine ($HS-CH_2-CH_2-NH_2$) is a small aminothiol molecule easily transported across cellular membranes, markedly reduces intralysosomal cystine accumulation and is currently approved as a treatment for cystinosis. Cysteamine can increase the cellular thiol and free thiol tripeptide glutathione pool, and thus modulate reactive oxygen species (ROS) scavenging, and decreased lipoperoxidation and glutathione peroxidase activity. Furthermore, cysteamine also increases adiponectin levels. Cysteamine is a precursor to the protein glutathione (GSH) precursor, and is currently FDA approved for use in the treatment of cystinosis, an intra-lysosomal cystine storage disorder. In cystinosis, cysteamine acts by converting cystine to cysteine and cysteine-cysteamine mixed disulfide which are then both able to leave the lysosome through the cysteine and lysine transporters respectively (Gahl et al., N Engl J Med 2002; 347(2):111-21). Within the cytosol the mixed disulfide can be reduced by its reaction with glutathione and the cysteine released can be used for further GSH synthesis. The synthesis of GSH from cysteine is catalyzed by two enzymes, gamma-glutamylcysteine synthetase and GSH synthetase. This pathway occurs in almost all cell types, with the liver being the major producer and exporter of GSH. The reduced cysteine-cysteamine mixed disulfide will also release cysteamine, which, in theory is then able to re-enter the lysosome, bind more cystine and repeat the process (Dohil et al., J Pediatr 2006; 148(6):764-9). In a study in children with cystinosis, enteral administration of cysteamine resulted in increased plasma cysteamine levels, which subsequently caused prolonged efficacy in the lowering of leukocyte cystine levels (Dohil et al., J Pediatr 2006; 148 (6):764-9). Cysteamine is addressed in International Patent Application Nos. WO 2009/070781, and WO 2007/089670, and U.S. Patent Publication Nos. 20110070272, 20090048154, and 20050245433.

Cystamine has the structure $H_2N-CH_2-CH_2-S-S-CH_2-CH_2-NH_2$. It should be readily apparent that cystamine can be reduced at the sulfide bond to for two molecules of cysteamine, which can then be processed and used by cells and the body as described above. Cystamine is generally handled as the dihydrochloride salt, $C_4H_{12}N_2S_2 \cdot 2HCl$.

SUMMARY

The disclosure provides a pharmaceutical dosage form, comprising a tablet or capsule, wherein the tablet of capsule comprises a core of, or is loaded with, a cysteamine salt or cystamine and wherein the tablet or capsule comprises an enteric coating thickness of 60-130 µm. In one embodiment, the tablet or capsule comprises from about 50 to about 300 mg of cysteamine base or cystamine. In another or further embodiment, the core or capsule further comprises one or more excipients. In another or further embodiment, the one or more excipients comprises a binder. In another or further embodiment, the core or capsule comprises cysteamine bitartrate. In another or further embodiment, the core or capsule comprises cysteamine-HCl. In another or further embodiment, the core or capsule consists of a cysteamine salt and less than 5% cystamine. In another or further embodiment, the core or capsule consists of cysteamine bitartrate. In another or further embodiment, the core or capsule consists of cysteamine-HCl. In another or further embodiment, the core or capsule consists of cysteamine salt and a binder. In another or further embodiment, the core or capsule comprises cystamine. In another or further embodiment, the core or capsule comprises cystamine dihydrochloride. In another or further embodiment, the core or capsule consists of cystamine. In another or further embodiment, the core or capsule consists of cystamine. In another or further embodiment, the core or capsule consists of cystamine and a binder. In another or further embodiment, the tablet is a monolithic tablet. In yet another or further embodiment, the capsule is a soft gel capsule. In still another or further embodiment, the tablet or capsule are a size 3 to size 00. In any of the foregoing embodiments, the enteric coating thicknesses increases as the dose and/or size of the tablet or capsule increases. In another or further embodiment, the tablet or capsule is resistant to mechanical degradation due to stomach motility. In another or further embodiment, the enteric coating thickness increases from about 75 µm for a 50 mg cysteamine base dose tablet or capsule to about 105 µm for a 150 mg cysteamine base dose tablet or capsule. In still another or further embodiment, the 50 mg dosage form is a size 4 tablet or capsule. In another embodiment, the 150 mg dosage form is a size 0 tablet or capsule. In another or further embodiment, the enteric-coated tablet or capsule are acid resistance such that not more than 10% of the cysteamine salt or cystamine in the core or capsule is release after a period of two hours or longer in a 0.1N HCl solution. In another or further embodiment, the enteric coating of the enteric-coated tablet or capsule dissolves such that 80% of the cysteamine salt or cystamine is released within 20 minutes in a solution buffered at pH 6.8.

The disclosure provides pharmaceutical dosage capsule containing about 50-150 mg cysteamine salt or cystamine, wherein the capsule comprises an enteric coating of about 60-130 µm thick. In another embodiment, the capsule contains about 50 mg of cysteamine base and has an enteric coating of about 60-100 µm thick. In another embodiment, the capsule contains about 50 mg of cystamine and has an enteric coating of about 60-100 µm thick. In another embodiment, the capsule contains about 50 mg of cysteamine base and has an enteric coating of about 70-80 µm thick. In another embodiment, the capsule contains about 50 mg of cystamine and has an enteric coating of about 70-80 µm thick. In another embodiment, the capsule contains about 150 mg of cysteamine base and has an enteric coating of about 100-130 µm thick. In another or further embodiment, the capsule contains about 150 mg of cystamine and has an enteric coating of about 100-130 µm thick. In another embodiment, the capsule contains about 150 mg of cysteamine base and has an enteric coating of about 100-110 µm thick. In yet another embodiment, the capsule contains about 150 mg of cystamine and has an enteric coating of about 100-110 µm thick.

The disclosure provides a pharmaceutical dosage tablet comprising about 50-150 mg cysteamine salt or cystamine, wherein the tablet comprises an enteric coating of about 60-130 µm thick. In one embodiment, the tablet comprises about 50 mg of cysteamine base and has an enteric coating of about 60-100 µm thick. In yet another embodiment, the tablet comprises about 50 mg of cystamine and has an enteric coating of about 60-100 µm thick. In still another embodiment, the tablet comprises about 50 mg of cysteamine base and has an enteric coating of about 70-80 µm thick. In another embodiment, the tablet comprises about 50 mg of cystamine and has an enteric coating of about 70-80 µm thick. In yet another embodiment, the tablet comprises about 150 mg of cysteamine base and has an enteric coating of about 100-130 µm thick. In still another embodiment, the tablet comprises about 150 mg of cystamine and has an enteric coating of about 100-130 µm thick. In another embodiment, the tablet comprises about 150 mg of cysteamine base and has an enteric coating of about 100-110 µm thick. In yet another embodiment, the tablet comprises about 150 mg of cystamine and has an enteric coating of about 100-110 µm thick.

In another embodiment of any of the foregoing, the capsule is an HPMC capsule and the enteric coating is Eudgrit.

In another embodiment of any of the foregoing, the pharmaceutical dosage form when delivered provides a 10-80 µmol plasma cysteamine level that results in a reduction in white cell cystine levels of about 0.5-1.0 for 6 to 12 hours.

DETAILED DESCRIPTION

As used herein and in the appended claims, the singular forms "a," "and," and "the" include plural referents unless the context clearly dictates otherwise. Thus, for example, reference to "a derivative" includes a plurality of such derivatives and reference to "a subject" includes reference to one or more subjects and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The term "about" as used herein can allow for a degree of variability in a value or range, for example, within 10%, within 5%, or within 1% of a stated value or of a stated limit of a range. When a range or a list of sequential values is given, unless otherwise specified any value within the range or any value between the given sequential values is also disclosed.

The term "substantially" as used herein refers to a majority of, or mostly, as in at least about 51%, 60%, 70%, 80%, 90%, 95%, 96%, 97%, 98%, 99%, 99.5%, 99.9%, 99.99%, or at least about 99.999% or more.

Unless defined otherwise, all technical and scientific terms used herein have the same meaning as commonly understood by one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

Cysteamine is an attractive candidate for the treatment of various diseases including cystinosis, Huntington's disease, Non-alcoholic fatty liver disease (NAFLD), Non-alcoholic steatohepatitis (NASH), eosinophilic disorders, insulin and diabetes, cancer and many more. This is in part due to a number of biological activities associated with cysteamine including modulating redox levels and due to its ability to react with cystine to produce cysteine, which can further be metabolized into glutathione, a potent endogenous antioxidant.

Cysteamine, however, is a potent gastric acid-secretagogue that has been used at very high doses in laboratory animals to induce duodenal ulceration; studies in humans and animals have shown that cysteamine-induced gastric acid hypersecretion is most likely mediated through hypergastrinemia. In previous studies performed in children with cystinosis who suffered regular upper gastrointestinal symptoms, a single oral dose of cysteamine (11-23 mg/kg) was shown to cause hypergastrinemia and a 2 to 3-fold rise in gastric acid-hypersecretion, and a 50% rise in serum gastrin levels. Symptoms suffered by these individuals included abdominal pain, heartburn, nausea, vomiting, and anorexia. U.S. Pat. No. 8,026,284 and published International Publication No. WO 2007/089670, both claiming priority to U.S. Provisional Patent application No. 60/762,715, filed Jan. 26, 2006, (all of which are incorporated by reference herein in their entirety) showed that cysteamine induced hypergastrinemia arises, in part, as a local effect on the gastric antral-predominant G-cells in susceptible individuals. The data also suggest that this is also a systemic effect of gastrin release by cysteamine. Depending on the route of administration, plasma gastrin levels usually peak after intragastric delivery within 30 minutes whereas the plasma cysteamine levels peak later.

Subjects with cystinosis are required to ingest oral cysteamine (CYSTAGON®; cysteamine bitartrate) every 6 hours day and night or use an enteric form of cysteamine (PROCYSBI®) every 12 hours. When taken regularly, cysteamine can deplete intracellular cystine by up to 90% (as measured in circulating white blood cells), and this had been shown to reduce the rate of progression to kidney failure/transplantation and also to obviate the need for thyroid replacement therapy. Because of the difficulty in taking CYSTAGON®, reducing the required dosing improves the adherence to therapeutic regimen. International Publication No. WO 2007/089670 demonstrates that delivery of cysteamine to the small intestine reduces gastric distress and ulceration, increases $C_{max}$ and increases AUC. Delivery of cysteamine into the small intestine is useful due to improved absorption rates from the small intestine, and/or less cysteamine undergoing hepatic first pass elimination when absorbed through the small intestine. A decrease in leukocyte cystine was observed within an hour of treatment.

Moreover, a pilot trial by Dohil et al. in 11 children with biopsy-confirmed NAFLD received enteric-coated (EC) cysteamine bitartrate orally for 24 weeks. This therapy resulted in statistically significant reductions in mean serum levels of alanine aminotransferase (ALT), aspartate aminotransferase (AST), total adiponectin, leptin, and cytokeratin-18 fragments, but without a concomitant reduction in body mass index. Seven out of 10 subjects reached the primary endpoints (of at least 50% reduction in ALT), the reduction in mean ALT and AST levels persisted 16 weeks after treatment ended. Triglyceride levels showed a trend to improvement by 30-40% although the population size of the study was small, the data is encouraging.

PROCYSBI® is a granulated form of cysteamine bitartrate that provides use in the treatment of infants and juveniles. However, due to the formulation, the amount of cysteamine base is limited to 25-75 mg of base per capsule (PROCYSBI, see, e.g., package insert). As the patient advances in age and size the number of capsules that must be taken increases and thus, what may be a few capsules of PROCYSBI as an infant, amounts to a maintenance dose of ~13 capsules every 12 hours for an adult with cystinosis. Thus, there is a need for a formulation that allows for fewer capsules while maintaining sufficient delivery for treating the disease or disorder. A reduction in capsules will also assist in patient compliance.

The disclosure thus provides a delayed and extended release tablet or capsule form of cysteamine salt or cystamine salt. As used herein, "capsule" refers to a solid pharmaceutical oral dosage form wherein the active (and inactive) ingredient are loaded into a hard or soft shell. The active and inactive ingredients are loaded in a relatively stable shell known as a capsule, allowing them to, for example, be taken orally or be used as suppositories. The two main types of capsules include hard-shelled capsules, which are typically made using gelatin and contain dry, Powdered ingredients or miniature pellets made by, e.g. processes of extrusion or spheronisation. These are made in two halves: a lower-diameter "body" that is filled and then sealed using a higher-diameter "cape". The second main type of capsules include soft-shelled capsules, primarily used for oils and for active ingredients that are dissolved or suspended in oil. Both of these classes of capsules are made from aqueous solutions of gelling agents like such as animal protein mainly gelatin; and plant polysaccharides or their derivatives like carrageenans and modified forms of starch and cellulose. Other ingredients can be added to the gelling agent solution like plasticizers such as glycerin and/or sorbitol to decrease the capsule's hardness, coloring agents, preservatives, disintegrants, lubricants and surface treatment.

As used herein, "tablet" refers to a pharmaceutical dosage form that includes a mixture of active substances and excipients, usually in powder form, pressed or compacted from a powder into a solid dose. The excipients can include diluents, binders or granulating agents, glidants (flow aids) and lubricants to ensure efficient tabletting; disintegrants to promote tablet break-up in the digestive tract; sweeteners or flavours to enhance taste; and pigments to make the tablets visually attractive.

In one embodiment, the composition is a tablet comprising a core of cysteamine salt or cystamine salt and one or more excipients that is then coated with or encapsulated within an enteric coating. In another embodiment, the composition is a capsule comprising cysteamine salt or cystamine salt loaded into the capsule body, wherein the capsule is then coated with or encapsulated by an enteric coating. The amount of cysteamine base can be from 50 mg to 500 mg per tablet or capsule, typically about 50-300 mg per table or capsule. The amount of cysteamine base can be from 50 mg to 500 mg per tablet or capsule, typically about 50-300 mg per tablet or capsule.

The delayed and extended release tablet or capsule comprises an enteric coating that ranges and increases in thickness from the lower dose tablet or capsule to the higher dose tablet or capsule. For example, a lower dose tablet or capsule of 50 mg cysteamine base or cystamine comprises an enteric coating on average of about 75 μm thick (e.g., from about 60-100 μm thick). A tablet or capsule comprising about 150 mg of cysteamine base or cystamine comprise an enteric coating on average of about 105 μm thick (e.g., 80-130 μm). The relationship between dose and thickness of the enteric coating is substantially linear. The thickness of the coating is designed to be thick enough to hold up to the mechanical actions of the upper gastrointestinal track and to delay release of the cysteamine or cystamine salt at a pH of about 4.5-6.5 (e.g., beginning at a pH of about 4.5). The tablets are dosed to a subject to obtain a circulating plasma level of cysteamine of about 10-80 μmol. Examples of capsules that can be coated can be found at Capsugel's website ([www].capsugel.com).

In another embodiment, the weight gain following coating of, for example, a 50 mg tablet or capsule is about 12.6% and about 10.8% for the 150 mg tablet or capsule. These weight gains correspond to about 11.19% and 9.75% coat levels, respectively. Taking into account the calculated volume of the capsules, the coat levels can be converted to coat thickness. Capsule dimensions can be obtained from manufacturers of such capsules (e.g., on commercially available websites, such as the Capsugel website). For example, a capsule of Size 4 was used for 50 mg capsules and Size 0 was used for 150 mg capsules. The average weights of the filled capsules were 225 mg for the 50 mg dose and 625 mg for the 150 mg dose. Assuming a specific gravity of 1.2 for the enteric coating, the estimated thickness of the coatings were ~77 μm and ~104 μm for the 50 and 150 mg capsules, respectively. It should be recognized that the coating thickness is not perfectly uniform over the whole of the tablet or capsule, but can vary by 10%, 9%, 8%, 7%, 6%, 5%, 4%, 3%, 2%, 1% or less. In one embodiment, the difference in enteric membrane thickness from tablet to tablet or capsule to capsule for a particular dosage (e.g., 50 mg) can be in a range of ±1-5% based on the total weight of the capsule or tablet.

In one embodiment, the absorption (AUC) of the dosage form when dosed orally is advantageously increased, compared to other dosage forms of cysteamine or cystamine by (a) reducing the number of tablets or capsules taken, while (b) influencing the absorption due to variations on tablet or capsule thickness thereby not only providing a delayed release (e.g., in the small intestine), but also providing an extended release (e.g., throughout the small intestine). The extended release is due, in part, to the thickness of different coatings on different sized tablets or capsules. For example, for cystinosis patients weighing more than 51 Kg a maintenance dose is about 1000 mg every 12 hours. Assuming that a tablet of the disclosure comprises 50 mg or 150 mg cysteamine base, this would result in the subject taking six 150 mg tablets and two 50 mg tablets, each of the 150 mg and 50 mg tablets have different enteric coating thicknesses thereby resulting in different dissolution times in the small intestine. For example it is contemplated that for 50 mg tablets or capsules, which have a thinner coating, the coating will dissolve earlier in the small intestine to release the cystamine or cysteamine, whereas for tablets or capsules with a thicker coating (e.g., 150 mg tablets) the coating will take longer to completely dissolve and release the cystamine or cysteamine composition. It is also important to recognize that a 1000 mg dose of PROCYSBI would require approximately 13 capsules of enterically coated granules.

As mentioned above, the tablet includes a core comprising cysteamine salt or cystamine salt. If the tablet comprises cysteamine salt the tablet includes less than 5% by weight of cystamine contaminants. If the composition comprises a capsule, the capsule is loaded with or comprises cysteamine salt or cystamine. The capsule may contain a granulated or powder form of cysteamine or cystamine salt. If the capsule includes cysteamine salt the capsule includes less than 5% by weight of cystamine contaminants.

Moreover, core tablet or capsule composition can comprise one or more excipients. For example, the excipients can include one or more fillers, binders, and surfactants. Other optional ingredients can include, but are not limited to, glidants, lubricants, disintegrants, swelling agents, and antioxidants.

Suitable fillers are known in the art and include, but are not limited to, lactose, saccharose, glucose, starch, microcrystalline cellulose, microfine cellulose, mannitol, sorbitol, calcium hydrogen phosphate, aluminum silicate, amorphous silica, and sodium chloride, starch, and dibasic calcium phosphate dehydrate. In one type of embodiment, the filler is not water soluble, although it may absorb water. In one embodiment, the filler includes microcrystalline cellulose.

Suitable binders are known in the art and include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, hydroxyethyl cellulose, and the like), and Veegum.

Lubricants used in the pharmaceutical arts are known. Such lubricants include, but are not limited to, magnesium stearate, calcium stearate, and stearic acid, and are typically present at no more than approximately 1 weight percent relative to tablet weight.

Disintegrants can also be used in the compositions of the disclosure. Disintegrants are used to facilitate tablet disintegration or "breakup" after administration, and are generally starches, clays, celluloses, algins, gums or crosslinked polymers.

If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like.

If desired, flavoring, coloring and/or sweetening agents may be added or coated on the tablet or capsule (typically on the enteric coating) as well. Other optional components for incorporation into an oral formulation herein include, but are not limited to, preservatives, suspending agents, thickening agents, and the like.

Various surfactants usable in the formulations and compositions of the disclosure are known in the art and include, but are not limited to, anionic surfactants, including sodium lauryl sulfate, sodium deoxycholate, dioctyl sodium sulfosuccinate, and sodium stearyl fumarate, nonionic surfactants, including polyoxyethylene ethers, and polysorbate 80, and cationic surfactants, including quaternary ammonium compounds. In one embodiment the surfactant is selected from anionic surfactants, e.g. sodium lauryl sulfate.

The amount of cysteamine free base in the core tablet or contained in the capsule can be at least 10 wt. % or at least 15 wt. %, or at least 20 wt. %, or at least 25 wt. %, or at least 30 wt. %. For example, the amount of cysteamine bitartrate can be at least 50 wt. %, or at least 55 wt. %, or at least 60 wt. %, or at least 65 wt. %, or at least 70 wt. %, or at least 75 wt. %, or at least 80 wt. %, or at least 85 wt. % of the core tablet or contained in the capsule, for example in a range of about 60 wt. % to about 90 wt. % or about 65 wt. % to about 85 wt. %. It is understood that any and all ranges including these values as endpoints is contemplated, for example, at least about 15 wt. % to about 90 wt. %, or at least about 20 wt. % to about 85 wt. %, or at least about 30 wt. % to about 85 wt. %, or at least about 50 wt. % to about 90 wt. %. As the dose of cysteamine free base can be up to about 2 $g/m^2$/day, and the amount of free base is relatively small compared to the molecular weight of salts (e.g. the bitartrate salt) it is desirable that the core tablet or capsule have as much active ingredient as possible while allowing the creation and processing of core particles. Moreover, because the "tablet" or "capsule" is enterically coated and not individual granulated or beads of the active ingredient the amount of active agent is increased on a per tablet or per capsule basis.

The amount of filler in the core tablet or contained in a capsule is not particularly limited. In embodiments, the amount of filler (e.g. microcrystalline cellulose) can be in a range of about 10 wt. % to about 30 wt. %, or about 16 wt. % to about 23 wt. %, or at least 19 wt. % or at least 19.5 wt. %, for example about 20 wt. %.

The amount of binder in the core tablet or contained in a capsule is not particularly limited. In embodiments, the amount of binder (e.g. hypromellose) can be in a range of about 1 wt. % to about 10 wt. %, or about 2 wt. % to about 8 wt. %, or about 4 wt. % to about 6 wt. %, for example about 5 wt. %.

The enteric coating material, e.g. polymer, can be one that will dissolve in intestinal juices at a pH level higher than that of the stomach, e.g. a pH of greater than 4.5, such as within the small intestine, and therefore permit release of the active substance in the regions of the small intestine and substantially not in the upper portion of the GI tract. In one embodiment, the enteric coating material begins to dissolve in at a pH between about 4.5 to about 5.5. In another embodiment, the enteric coating material can be designed to rapidly dissolve at a specific pH (i.e., a pH between 4.5 and 6.5).

The pH of the small intestine gradually increases from about 4.5 to about 6.5 in the duodenal bulb to about 7.2 in the distal portions of the small intestine (ileum). In order to provide predictable dissolution corresponding to the small intestine transit time of about 3 hours (e.g., 2-3 hours) and permit reproducible release therein, the membrane should begin to dissolve within the pH range of the duodenum, and continue to dissolve at the pH range within and throughout the small intestine. Therefore, the amount (thickness) of enteric coating should be sufficient to be substantially dissolved during the approximate three hour transit time within the small intestine (e.g., the proximal and mid-small intestine).

Enteric coating materials include, but are not limited to, one or more of the following: cross-linked polyvinyl pyrrolidone; non-cross linked polyvinylpyrrolidone; hydroxypropylmethyl cellulose phthalate, hydroxypropylmethyl cellulose acetate succinate, cellulose acetate succinate; cellulose acetate phthalate, hydroxypropylmethyl cellulose acetate succinate, cellulose acetate trimellitate; starch acetate phthalate; polyvinyl acetate phthalate; carboxymethyl cellulose; methyl cellulose phthalate; methyl cellulose succinate; methyl cellulose phthalate succinate; methyl cellulose phthalic acid half ester; ethyl cellulose succinate; carboxymethylamide; potassium methacrylatedivinylbenzene copolymer; polyvinylalcohols; polyoxyethyleneglycols; polyethylene glycol; sodium alginate; galactomannone; carboxypolymethylene; sodium carboxymethyl starch; copolymers of acrylic acid and/or methacrylic acid with a monomer selected from the following: methyl methacrylate, ethyl methacrylate, ethyl acrylate, butyl methacrylate, hexyl methacrylate, decyl methacrylate, lauryl methacrylate, phenyl methacrylate, methyl acrylate, isopropyl acrylate, isobutyl acrylate, or octadecyl acrylate, e.g. EUDRAGIT-L and -S series, including L 100-55, L 30 D-55, L 100, S 100, L 12.5, and S 12.5, available from Evonik Industries; polyvinyl acetate; fats; oils; waxes; fatty alcohols; shellac; zein; gluten; ethylacrylate-maleic acid anhydride copolymer; maleic acid anhydride-vinyl methyl ether copolymer; styrol-maleic acid copolymer; 2-ethyl-hexylacrylate maleic acid anhydride; crotonic acid-vinyl acetate copolymer; glutaminic acid/glutamic acid ester copolymer; carboxymethylethylcellulose glycerol monooctanoate; polyarginine; poly(ethylene); poly(propylene); poly(ethylene oxide); poly(ethylene terephthalate); poly(vinyl isobutyl ether); poly(vinyl chloride); and polyurethane. A combination of enteric coating material may also be used. For example, the enteric material can be selected from a copolymer of methacrylic acid and methyl methacrylate, and a copolymer of methacrylic acid and ethyl acrylate. For example, an enteric polymer is poly(methacrylic acid co-ethyl acrylate) 1:1 (EUDRAGIT L 30 D-55 and EUDRAGIT L100-55).

Examples of some enteric coatings are disclosed in U.S. Pat. No. 5,225,202, including beeswax and glyceryl monostearate; beeswax, shellac and cellulose; and cetyl alcohol, mastic and shellac, as well as shellac and stearic acid (U.S. Pat. No. 2,809,918); polyvinyl acetate and ethyl cellulose (U.S. Pat. No. 3,835,221); and neutral copolymer of polymethacrylic acid esters (Eudragit L30D) (F. W. Goodhart et al., Pharm. Tech., pp. 64-71, April 1984); copolymers of methacrylic acid and methacrylic acid methylester (Eudragits), or a neutral copolymer of polymethacrylic acid esters containing metallic stearates (Mehta et al., U.S. Pat. Nos. 4,728,512 and 4,794,001). Such coatings comprise mixtures of fats and fatty acids, shellac and shellac derivatives and the cellulose acid phthlates, e.g., those having a free carboxyl content. See also Remington's Pharmaceutical Sciences, A. Osol, ed., Mack Pub. Co., Easton, Pa. (16th ed. 1980) at pages 1590-1593, and Zeitova et al. (U.S. Pat. No. 4,432,966), for descriptions of suitable enteric coating compositions.

One or more plasticizers can be added to enteric coating material in order to increase their pliability and reduce brittleness, as it is known in the art. Suitable plasticizers are known in the art and include, for example, butyl citrates, triethyl citrate, diethyl phthalate, dibutyl sebacate, PEGs (e.g. PEG 6000), acetyl triethyl citrate, and triacetin. In one type of embodiment, the plasticizer is triethyl citrate. While some enteric materials are flexible and do not require addition of plasticizers, more brittle polymers (e.g., Eudragit L/S types, Eudragit RL/RS, and Eudragit FS 30 D) benefit from plasticizers, e.g. in the range of 5 wt. % to 30 wt. % based on the dry polymer mass, e.g. about 8 wt. % to about 12 wt. % triethyl citrate with poly(methacrylic acid co-ethyl acrylate) 1:1.

One or more anti-tacking agents (antiadherents) can also be added to an enteric coating material in order to reduce the tackiness of the film and prevent agglomeration, as it is known in the art. Anti-tacking agents include talc, and glyceryl monostearate, fumed silica (e.g., AEROSIL 200), precipitated silica (e.g., SIPERNAT PQ), and magnesium stearate, for example. Anti-tacking agents can be used in any suitable quantity, for example in a range of about 10 wt. % to 100 wt. % based on dry polymer mass, or about 10 wt. % to about 50 wt. %, or about 10 wt. % to about 30 wt. %, or about 15 wt. % to about 30 wt. %. For example, in one embodiment the amount of talc is in a range of 15 wt. % to about 30 wt. %, based on dry polymer mass.

The enteric coating material can be formed by any suitable process. Coating processes include pan coating, fluid bed coating, and dry coating (e.g., heat dry coating and electrostatic dry coating), for example. Pan coating and fluid bed coating using solvent are well established processes. In liquid coating, the enteric coating material and optional excipients (e.g., pigments, plasticizers, anti-tacking agents) are mixed in an organic solvent or water to form a solution or dispersion. The coating solution or dispersion is sprayed into solid dosage forms in a pan coater or a fluid bed dryer and dried by hot air. For example, in a Wurster fluid bed coating process, the coating fluid is sprayed from the bottom of the fluid bed apparatus, whereas in an alternative the coating fluid is applied by top spraying, and in another alternative tangential spray is applied.

The amount of enteric coating material applied is sufficient to achieve desired acid resistance and release characteristics. For example, in one embodiment the amount of enteric coating will be sufficient to meet United States Pharmacopeia (USP)<711> requirements (USP 36-NF 31) for delayed-release dosage forms, thereby not releasing 10.0 wt. % of drug after 2 hours in 0.1N HCl. In another aspect, the formulation will be sufficient to release at least 80% of the active in 20 minutes in pH 6.8 buffer solution, e.g. using the dissolution method of USP 36-NF 31 section <711>. In one embodiment, amount of enteric coating on the tablets or capsules will be sufficient to provide a pharmacokinetic profiles indicative of release in and throughout the small intestine. In a further embodiment, the thickness of the enteric coating is about 75 µm for a 50 mg tablet or capsule and about 105 µm for a 150 mg tablet or capsule.

The capsule shell that can be used in the compositions of the disclosure and that are enterically coated include both soft and hard capsule shells. In one embodiment, the capsule shell is a hard capsule shell, e.g. a gelatin capsule shell or a vegetable-based hard capsule shell.

Thus, for example, one embodiment of the disclosure provides a tablet comprising a 50 mg of cysteamine base or cystamine that may include a binder and/or other excipients as described above, wherein the tablet is enterically coated to a thickness of about 60-100 µm, typically about 70-80 µm and commonly about 75 µm. In some embodiments, the tablet is of a size 3-5, and typically a size 4 and comprises 50 mg of cysteamine base or cystamine and an enteric coating of 60-100 µm thick.

In another embodiment of the disclosure a tablet comprising a 150 mg of cysteamine base or cystamine that may include a binder and/or other excipients as described above, wherein the tablet is enterically coated to a thickness of about 80-130 µm, typically about 95-115 µm and commonly about 105 µm. In some embodiments, the tablet is of a size 1 to 00, but typically is a size 0, and comprises 150 mg of cysteamine base or cystamine and an enteric coating of 80-130 µm thick.

In yet another embodiment of the disclosure a capsule filled with or comprises 50 mg of cysteamine base or cystamine that may include a binder and/or other excipients as described above is provided, wherein the capsule is enterically coated to a thickness of about 60-100 µm, typically about 70-80 µm and commonly about 75 µm. In some embodiments, the capsule is of a size 3-5, and typically a size 4 and comprises 50 mg of cysteamine base or cystamine and an enteric coating of 60-100 µm thick.

In still another embodiment of the disclosure a capsule is filled with or comprises 150 mg of cysteamine base or cystamine that may include a binder and/or other excipients as described above, wherein the capsule is enterically coated to a thickness of about 80-130 µm, typically about 95-115 µm and commonly about 105 µm. In some embodiments, the capsule is of a size 1 to 00, but typically is a size 0, and comprises 150 mg of cysteamine base or cystamine and an enteric coating of 80-130 µm thick.

Various of the features described above includes a pharmaceutical dosage form including a core tablet or capsule containing or comprising cysteamine bitartrate, cysteamine-HCL or cystamine, a filler (optionally microcrystalline cellulose), a binder (optionally hypromellose), and an enteric coating (optionally Eudragit L30 D-55) surrounding the tablet core or capsule, wherein the enteric coating has a thickness that increase from about 60 µm to about 130 µm as the dose of cysteamine bitartrate increases (e.g., from a size 1 to size 00 tablet or capsule).

In one embodiment, the enteric formulation(s) of the disclosure comprising cysteamine salt or cystamine provide a mean $T_{max}$ upon oral dosing, fasted, of greater than 75 minutes, or at least 110 minutes, or at least 2 hours, or at least 3 hours, or in a range of about 2.2 hours to about 3.48 hours, or about 2.22 hours to about 3.34 hours, or about 2.78 hours, or a $T_{max}$ in a range of 80% to 125%, or 80% to 120% of such reference $T_{max}$.

In another embodiment, the enteric formulation(s) of the disclosure comprising cysteamine salt or cystamine provides a mean $C_{max}$ upon oral dosing, fasted, in a range of about 22.16 µmol/L to about 34.63 µmol/L, or about 22.16 µmol/L to about 33.24 µmol/L, or about 22.7 µmol/L, normalized to a 450 mg dose, or a $C_{max}$ in a range of 80% to 125%, or 80% to 120% of such reference $C_{max}$.

In another embodiment, the enteric formulation(s) of the disclosure comprising cysteamine salt or cystamine provides a mean AUC (0-6 hours) upon oral dosing, fasted, in a range of about 60.74 µmol/L to about 94.91 µmol/L, or about 60.74 µmol/L to about 91.12 µmol/L, or about 75.93 µmol/L, normalized to a 450 mg dose, or a bioequivalent AUC (0-6 hours) in a range of 80% to 125%, or 80% to 120% of such reference AUC (0-6 hours). In another embodiment, the enteric formulation(s) of the disclosure comprising cysteamine salt or cystamine provides a mean AUC (0-12 hours) upon oral dosing in a range of about 79.41 µmol/L to about 124.08 µmol/L, or about 79.41 µmol/L to about 119.11 µmol/L, or about 99.26 µmol/L, normalized to a 450 mg dose, or a bioequivalent AUC (0-12 hours) in a range of 80% to 125%, or 80% to 120% of such reference AUC (0-12 hours). In another embodiment, the enteric formulation(s) of the disclosure comprising cysteamine salt or cystamine provides a mean AUC (0-inf_D) upon oral dosing in a range of about 0.86 minmg/L/mg to about 1.35 minmg/L/mg, or about 0.86 minmg/L/mg to about 1.3 minmg/L/mg, or a bioequivalent AUC (0-inf_D) in a range of 80% to 125%, or 80% to 120% of such reference AUC (0-inf_D).

In another embodiment, the enteric formulation(s) of the disclosure comprising cysteamine salt or cystamine provides a mean pharmacokinetic parameters upon oral dosing, fasted, of: $T_{max}$ 183±90 minutes, $C_{max}$ 3.5±1.7 mg/L, and/or AUC (0-inf_D) 1.08±0.46 min*mg/L/mg, or a bioequivalent $T_{max}$, $C_{max}$ or AUC in a range of 80% to 125%, or 80% to 120% of such reference parameter. For examples, a dose of 450 mg of enteric coated capsules containing cysteamine bitartrate provides a $T_{max}$ of about 220 min and an AUC of about 5104 µM.

Also contemplated is a method for the preparation of an enteric formulation(s) of the disclosure comprising cysteamine salt or cystamine according to the disclosure, including coating a core tablet or capsule comprising or containing cysteamine or a pharmaceutically acceptable salt thereof or cystamine or a pharmaceutical salt thereof and an excipient with an enteric coating material to form an enterically coated tablet or capsule containing cysteamine or cystamine or salts thereof.

In one embodiment, tablets of cysteamine salt or cystamine or salt thereof can be obtained and compressed with or without additional excipients into a tablet (e.g., a monolithic tablet) and the tablet coated with an enteric coating. In one embodiment, the tablet includes a disintegrant or binder. In one embodiment, the cysteamine or cystamine product composition is administered in tablet form. Tablets are manufactured by first enterically coating the cysteamine or cystamine product. A method for forming tablets herein is by direct compression of the powders comprising cysteamine or cystamine product, optionally in combination with diluents, binders, lubricants, disintegrants, colorants, stabilizers or the like. As an alternative to direct compression, compressed tablets can be prepared using wet-granulation or dry-granulation processes. Tablets may also be molded rather than compressed, starting with a moist material containing a suitable water-soluble lubricant.

In another embodiment, cysteamine or salts thereof or cystamine or salt thereof is obtained and filled into a capsule to obtain the desired dose and the capsule is coated with an enteric material. The capsule may be filled with a powder form of the agent, granulated forms of the agent, or any other form of the active agent (i.e. cysteamine salt or cystamine).

The enteric coating can be applied to the tablet or capsule using standard techniques including, but not limited to, spray coating, dip-coating, pan coating, gas suspension coating, electrostatic coating and compression coating. The coating need not be perfectly uniform and a coating thickness may vary slightly from the desired coating thickness by 0%-10% of the thickness. In some instances the coating may be applied in multiple steps (e.g., a first coating followed by a second coating). In still other embodiments, the tablet or capsule may comprise different enteric coating materials that are layered to a desired thickness. For example, if the total thickness is 100 µm, a first enteric coating may be 5-95 µm thick and the second coating is the balance of the coating (i.e., 95-105 µm thick, respectively).

For administration of the dosage form, a total weight in the range of approximately 50 mg to 1000 mg (based on the free base) can be used. The dosage form can be orally administered to a patient suffering from a condition for which cysteamine is indicated, including, but not limited to, cystinosis and other metabolic and neurodegenerative diseases including non-alcoholic fatty liver disease (NAFLD) and other liver and biliary tract disorders, Huntingon's disease, Parkinson's disease, Rett Syndrome and others, use as free radical and radioprotectants, and as hepto-protectant agents. In any method described herein, the treatment of humans is contemplated. The compositions of the disclosure can be used in combination with other therapies useful for treating cystinosis and neurodegenerative diseases and disorders. For example, indomethacin therapy is an anti-inflammatory used to treat rheumatoid arthritis and lumbago, but it can be used to reduce water and electrolyte urine loss. In children with cystinosis, indomethacin reduces the urine volume and therefore liquid consumption by about 30%, sometimes by half. In most cases this is associated with an appetite improvement. Indomethacin treatment is generally followed for several years.

Moreover, the dosing of a subject with a disease treatable by cysteamine can include multiple tablets or capsules as described above. In one embodiment, the formulation and compositions provided herein are designed to include tablets or capsules of varying sizes between 50 mg to 500 mg of cysteamine base or cystamine. As such, a subject will take, e.g., orally capsules or tablets having different thicknesses and thereby resulting in different dissolution times in the small intestine and thereby effecting the pharmacokinetics.

Other therapies can be combined with the methods and compositions of the disclosure to treat diseases and disorders that are attributed or result from cystinosis. Urinary phosphorus loss, for example, entails rickets, and it may be necessary to give a phosphorus supplement. Carnitine is lost in the urine and blood levels are low. Carnitine allows fat to be used by the muscles to provide energy. Hormone supplementation is sometimes necessary. Sometimes the thyroid gland will not produce enough thyroid hormones. This is given as thyroxin (drops or tablets). Insulin treatment is sometimes necessary if diabetes appears, when the pancreas does not produce enough insulin. These treatments have become rarely necessary in children whom are treated with cysteamine, since the treatment protects the thyroid and the pancreas. Some adolescent boys require a testosterone treatment if puberty is late. Growth hormone therapy may be indicated if growth is not sufficient despite a good hydro electrolytes balance. Accordingly, such therapies can be combined with the compositions and methods disclosed herein.

The effectiveness of a method or composition of the disclosure can be assessed by measuring leukocyte cystine concentrations, cytokeratin-18 (in the case of NAFLD or NASH) or other markers of the disease being treated. Dosage adjustment and therapy can be made by a medical specialist depending upon, for example, the concentration of the marker (e.g., cystine in leukocytes) and the ability to tolerate the drug. The dose is typically adjusted to the highest tolerable dose (e.g., about 10-80 µmol of plasma cysteamine). Additional therapies including the use of omeprazole can reduce side effects of cysteamine administration, such as abdominal pain, heartburn, nausea, vomiting, and anorexia, which can result from cysteamine-induced gastric acid hypersecretion, for example.

In various embodiments of the disclosure, the cysteamine or cystamine composition of the disclosure is administered at a daily dose ranging from about 10 mg/kg to about 2.5 g/kg, or from about 100 mg/kg to about 250 mg/kg, or from about 60 mg/kg to about 100 mg/kg or from about 50 mg/kg to about 90 mg/kg, or from about 30 mg/kg to about 80 mg/kg, or from about 20 mg/kg to about 60 mg/kg, or from about 10 mg/kg to about 50 mg/kg. Further, the effective dose may be 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, 225 mg/kg, 250 mg/kg, 275 mg/kg, 300 mg/kg, 325 mg/kg, 350 mg/kg, 375 mg/kg, 400 mg/kg, 425 mg/kg, 450 mg/kg, 475 mg/kg, 500 mg/kg, 525 mg/kg, 550 mg/kg, 575 mg/kg, 600 mg/kg, 625 mg/kg, 650 mg/kg, 675 mg/kg, 700 mg/kg, 725 mg/kg, 750 mg/kg, 775 mg/kg, 800 mg/kg, 825 mg/kg, 850 mg/kg, 875 mg/kg, 900 mg/kg, 925 mg/kg, 950 mg/kg, 975 mg/kg or 1000 mg/kg, or may range between any two of the foregoing values. In some embodiments, the cysteamine or cystamine composition is administered at a total daily dose of from approximately 0.25 g/m$^2$ to 4.0 g/m$^2$ body surface area, about 0.5-2.0 g/m$^2$ body surface area, or 1-1.5 g/m$^2$ body surface area, or 1-1.95 g/m$^2$ body surface area, or 0.5-1 g/m$^2$ body surface area, or about 0.7-0.8 g/m$^2$ body surface area, or about 1.35 g/m$^2$ body surface area, or about 1.3 to about 1.95 grams/m$^2$/day, or about 0.5 to about 1.5 grams/m$^2$/day, or about 0.5 to about 1.0 grams/m$^2$/day, e.g., at least about 0.3, 0.4, 0.5, 0.6, 0.7, 0.8, 0.9, 1.0, 1.1, 1.2, 1.3, 1.4, 1.5, 1.6, 1.7, 1.8, 1.9 or 2 g/m$^2$, or up to about 0.8, 0.9, 1.0, 1.1, 1.2, 1.3, 1.4, 1.5, 1.6, 1.7, 1.8, 1.9, 2.0, 2.2, 2.5, 2.7, 3.0, 3.25, 3.5 or 3.75 g/m$^2$ or may range between any two of the foregoing values.

In some embodiments, the delayed and extended release formulation comprises an enteric coating that releases the cysteamine or cystamine when the formulation reaches the small intestine or a region of the gastrointestinal tract of a subject in which the pH is greater than about pH 4.5. In various embodiments, the formulation releases at a pH of about 4.5 to 6.5, 4.5 to 5.5, 5.5 to 6.5 or about pH 4.5, 5.0, 5.5, 6.0 or 6.5.

Pharmaceutically acceptable salts of cysteamine or cystamine compositions include pharmaceutically-acceptable anions and/or cations. Pharmaceutically-acceptable cations include among others, alkali metal cations (e.g., Li$^+$, Na$^+$, K$^+$), alkaline earth metal cations (e.g., Ca$^{2+}$, Mg$^{2+}$), non-toxic heavy metal cations and ammonium (NH$^{4+}$) and substituted ammonium (N(R')$^{4+}$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., Cl$^-$, Br$^-$), sulfate, acetates (e.g., acetate, trifluoroacetate), ascorbates, aspartates, benzoates, citrates, and lactate.

The following references provide one of skill with a general definition of many of the terms used in this disclosure: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

It is to be understood that while the disclosure has been described in conjunction with specific embodiments thereof, that the foregoing description as well as the examples which follow are intended to illustrate and not limit the scope of the disclosure. Other aspects, advantages and modifications within the scope of the disclosure will be apparent to those skilled in the art to which the disclosure.

What is claimed:

1. A pharmaceutical dosage form, comprising a plurality of tablets or capsules of differing sizes and doses, wherein each of the tablet or capsule comprises a core of, or is loaded with, a cysteamine salt and/or cystamine at about 50 mg or about 150 mg and wherein each of the tablet or capsule comprises an enteric coating of poly(methacrylic acid co-ethyl acrylate at a 1:1 ratio and has a thickness of 60-130 µm and wherein thickness is different between tablets or capsules of differing sizes, wherein tablets or capsules containing about 50 mg of cysteamine salt and/or cystamine have a coating thickness of about 60-100 µm and wherein tablets or capsules containing about 150 mg of cysteamine salt and/or cystamine have a coating thickness of about 100-130 µm.

2. The pharmaceutical dosage form of claim 1, wherein each core or capsule in the plurality of tablets or capsules further comprises one or more excipients.

3. The pharmaceutical dosage form of claim 2, wherein the one or more excipients comprises a binder.

4. The pharmaceutical dosage form of claim 1, wherein each core or capsule in the plurality of tablets or capsules comprises cysteamine bitartrate.

5. The pharmaceutical dosage form of claim 1, wherein each core or capsule in the plurality of tablets or capsules comprises cysteamine-HCl.

6. The pharmaceutical dosage form of claim 1, wherein each core or capsule in the plurality of tablets or capsules consists of a cysteamine salt and less than 5% cystamine.

7. The pharmaceutical dosage form of claim 1, wherein each core or capsule in the plurality of tablets or capsules consists of cysteamine bitartrate or cysteamine-HCl.

8. The pharmaceutical dosage form of claim 1, wherein each core or capsule in the plurality of tablets or capsules comprises cystamine dihydrochloride.

9. The pharmaceutical dosage form of claim 1, wherein each core or capsule in the plurality of tablets or capsules consists of cystamine.

10. The pharmaceutical dosage form of claim 1, wherein each core or capsule in the plurality of tablets or capsules consists of cystamine and a binder.

11. The pharmaceutical dosage form of claim 1, wherein each tablet in the plurality of tablets or capsules is a monolithic tablet.

12. The pharmaceutical dosage form of claim 1, wherein each capsule in the plurality of tablets or capsules is a soft gel capsule.

13. The pharmaceutical dosage form of claim 1, wherein each tablet or capsule in the plurality of tablets or capsules are a size 3 to size 00.

14. The pharmaceutical dosage form of claim 1, wherein the enteric coating thicknesses increases as the dose of cysteamine salt and/or cystamine increases.

15. The pharmaceutical dosage form of claim 1, wherein each tablet or capsule in the plurality of tablets or capsules is resistant to mechanical degradation due to stomach motility.

16. The pharmaceutical dosage form of claim 1, wherein the enteric coating thickness increases from about 75 μm for a 50 mg cysteamine base dose tablet or capsule to about 105 μm for a 150 mg cysteamine base dose tablet or capsule.

17. The pharmaceutical dosage form of claim 16, wherein the 50 mg dosage form is a size 4 tablet or capsule.

18. The pharmaceutical dosage form of claim 16, wherein the 150 mg dosage form is a size 0 tablet or capsule.

19. The pharmaceutical dosage form of claim 1, wherein the plurality of tablets or capsules are acid resistance such that not more than 10% of the cysteamine salt and/or cystamine in each core or capsule of the plurality of tablets or capsules is released after a period of two hours or longer in a 0.1N HCl solution and/or wherein the enteric coating dissolves such that 80% of the cysteamine salt or cystamine is released within 20 minutes in a solution buffered at pH 6.8.

20. A pharmaceutical dosage capsule or tablet containing about 50 or about 150 mg cysteamine salt and/or cystamine, wherein the capsule comprises an enteric coating of poly (methacrylic acid co-ethyl acrylate at a 1:1 ratio, wherein the capsule or tablet containing about 50 mg of cysteamine salt and/or cystamine has an enteric coating of about 60-100 μm thick and wherein the capsule or tablet containing about 150 mg of cysteamine salt and/or cystamine has an enteric coating of about 100-130 μm thick.

21. The pharmaceutical dosage form of claim 1, wherein the pharmaceutical dosage form delivered to provide a 10-80 μmol plasma cysteamine level results in a reduction in white cell cystine levels of about 0.5-1.0 for 6 to 12 hours.

22. The pharmaceutical dosage form of claim 20, wherein the pharmaceutical dosage form delivered to provide a 10-80 μmol plasma cysteamine level results in a reduction in white cell cystine levels of about 0.5-1.0 for 6 to 12 hours.

* * * * *